(12) United States Patent
Frank et al.

(10) Patent No.: US 7,480,051 B2
(45) Date of Patent: Jan. 20, 2009

(54) APPARATUS AND METHOD FOR HARD-DOCKING A TESTER TO A TILTABLE IMAGER

(75) Inventors: Jonathan Frank, Los Gatos, CA (US); Rick Portune, Sunnyvale, CA (US)

(73) Assignee: DCG Systems, Inc., Fremont, CA (US)

( * ) Notice: Subject to any disclaimer, the term of this patent is extended or adjusted under 35 U.S.C. 154(b) by 344 days.

(21) Appl. No.: 11/054,094

(22) Filed: Feb. 10, 2005

(65) Prior Publication Data

US 2006/0176477 A1  Aug. 10, 2006

(51) Int. Cl.
*G01B 11/00* (2006.01)
(52) U.S. Cl. ..................................... 356/399
(58) Field of Classification Search ... 356/237.1–237.6, 356/399–401
See application file for complete search history.

(56) References Cited

U.S. PATENT DOCUMENTS

| | | | |
|---|---|---|---|
| 3,524,694 A | 8/1970 | Kelin | |
| 3,711,186 A | 1/1973 | O'Connor | |
| 3,912,378 A | 10/1975 | Goto | |
| 4,634,234 A | 1/1987 | Baumann | |
| 4,890,918 A * | 1/1990 | Monford | 356/150 |
| 5,004,307 A | 4/1991 | Kino et al. | |
| 5,208,648 A | 5/1993 | Batchelder | |
| 5,220,403 A | 6/1993 | Batchelder | |
| 5,282,088 A | 1/1994 | Davidson | |
| 5,475,316 A | 12/1995 | Hurley et al. | |
| 5,493,236 A | 2/1996 | Ishii et al. | |
| 5,940,545 A | 8/1999 | Kash et al. | |
| 6,252,412 B1 | 6/2001 | Talbot et al. | |
| 6,304,092 B1 * | 10/2001 | Jordan | 324/758 |
| 6,462,814 B1 | 10/2002 | Lo | |
| 6,509,750 B1 | 1/2003 | Talbot et al. | |
| 6,515,494 B1 | 2/2003 | Low | |
| 6,591,121 B1 | 7/2003 | Madarasz | |
| 6,621,275 B2 | 9/2003 | Cotton et al. | |
| 6,700,659 B1 * | 3/2004 | Chunduri et al. | 356/237.5 |
| 6,876,215 B1 * | 4/2005 | Hannan et al. | 324/758 |
| 2003/0112331 A1 | 6/2003 | Chen | |
| 2004/0119069 A1 | 6/2004 | Gemar et al. | |

* cited by examiner

*Primary Examiner*—Tarifur R. Chowdhury
*Assistant Examiner*—Isiaka O Akanbi
(74) *Attorney, Agent, or Firm*—Nixon Peabody LLP; Joseph Bach, Esq.

(57) ABSTRACT

An apparatus and method are disclosed for hard-docking of a tester head to a DUT, while permitting the angular alignment of a specimen to be inspected to the optical axis of an optical testing tool. In one example, a system for orthogonal alignment of a specimen to an optical axis of a collection optics is provided. The system comprises a self-leveling tabletop; a specimen holder coupled to the tabletop and held at a fix orientation; collection optics coupled to the tabletop; a plunger coupled to the tabletop and operable to maintain the leveling orientation of the tabletop; a control valve sensing the leveling orientation of the tabletop and coupled to the plunger to control the operation of the plunger; and an aligner coupled to the tabletop and operable to change the alignment of the optical axis of the collection optics with respect to the specimen without changing the fixed orientation of the specimen holder.

21 Claims, 10 Drawing Sheets

APPARATUS AND METHOD FOR HARD-DOCKING A TESTER TO A TILTABLE IMAGER

BACKGROUND OF THE INVENTION

1. Field of the Invention

The present invention relates to an apparatus and method for controlling the tilt of an imager to allow alignment to a specimen, while permitting a hard-dock to a tester connected to the specimen.

2. Description of the Related Art

Many optical systems for inspection of specimen, such as substrates, exist in the prior art. One such system is described in U.S. Pat. No. 6,621,275, which is assigned to the current assignee and which is incorporated herein by reference in its entirety. Such systems can be used for inspection or testing and debug of semiconductor substrates or integrated circuits. Examples of systems for imaging flip-chip type integrated circuits through the silicon substrate are described in U.S. Pat. Nos. 5,208,648, 5,220,403 and 5,940,545, which are incorporated herein by reference in their entirety.

Figure 1A:
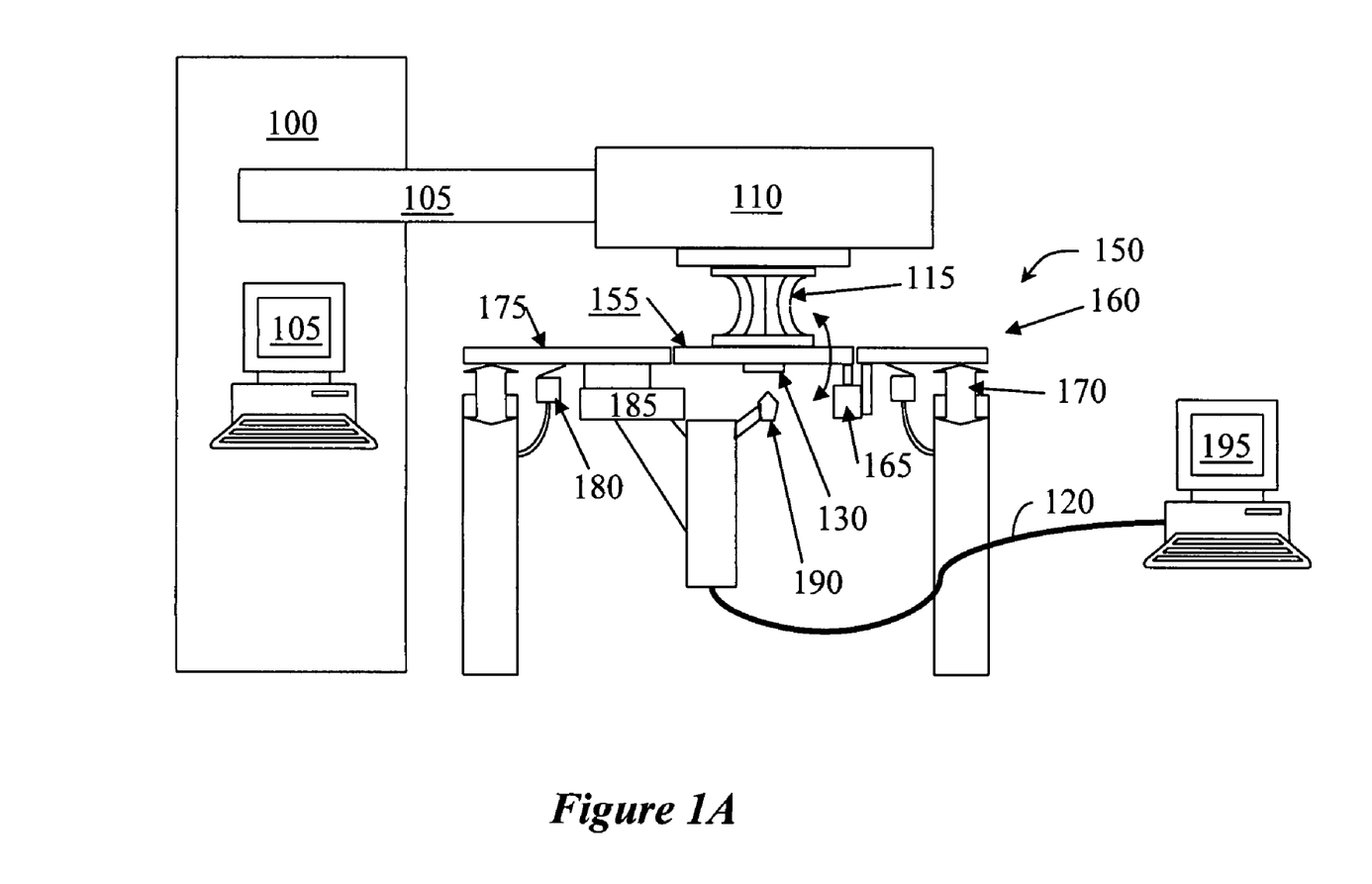
FIGS. 1A and 1B are general schematics depicting the major components of the testing and debug system according to the prior art.
Figure 1B:
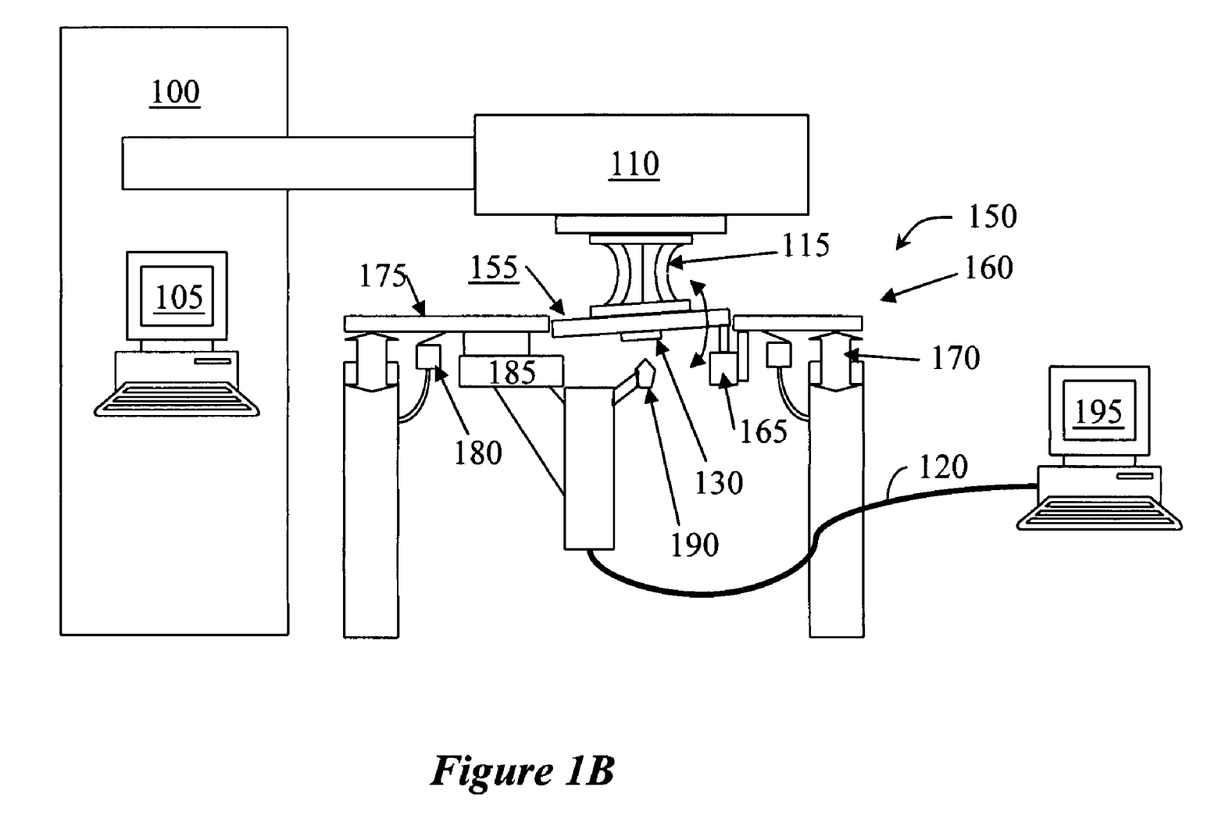

FIGS. 1A and 1B are general schematics depicting major components of an arrangement of an Automated Testing System (ATE) connected to an emission testing and debug system (Such as the Sapphire™ and the EmiScope™, respectively, available from Credence Systems, Inc. of Milpitas, Calif.) that is helpful for the understanding of the present invention. A system that is similar to the EmiScope is described in co-assigned U.S. patent application Ser. No. 10/912,896 which is incorporated herein by reference in its entirety. As will become apparent from the description, this arrangement is used to illustrate the features of the invention; however, the invention is not limited in its applicability to such an arrangement and is rather useful in various other systems and arrangements.

In FIGS. 1A and 1B, the ATE 100 is shown with its tester head 110 extended over the emission tester 150, so as to connect to a device under test (DUT) 130 via flexible connector 115. The tester head 110 is movable for docking using manipulation arm 105. The ATE 100 generally comprises a controller, such as a pre-programmed computer 105, that generates and delivers test signals to the DUT 130 in a manner well known in the art. Specifically, the ATE 100 is used to generate signals that stimulate the DUT 130 to perform various tasks, as designed by the chip designer to check and/or debug the DUT 130. The various signals generated by the controller 105 are delivered to the DUT 130 via the connector 115. As is well known in the art, as the DUT 130 reacts to the various test signals received from the ATE, the DUT's various active elements emit light. The light is then detected by the emission tester 150 and is used by the emission tester 150 to decipher the operation of the DUT 130.

On the emission tester side, the DUT 130 is held on an adapter plate 155, which is connected to a self-leveling, vibration-isolation bench 160 via tilting mechanism 165. The tilting mechanism 165 can be implemented using servomotors, or in other manners as described more fully in the above-cited co-assigned patent application. While only one tilting mechanism is shown, it should be appreciated that several can be used so as to obtain the appropriate degrees of freedom for the required tilting. The bench 160 can be any commercially available self-leveling vibration-isolation bench (e.g., the Precision-Aire™ available from Fabreeka™ of Boston, Mass. or an Optical Table 5000 series, available from Kinetic Systems, Inc. of Boston Mass.). Such a bench generally includes a tabletop 175 riding on plungers 170. Each plunger 170 is operable, pneumatically, for example, to rise or drop so as to level to tabletop 175. A level control valve 180 is used to control the plunger so as to provide automatic leveling of the tabletop 175. An x-y-z stage 185 is connected to the underside of the tabletop 175. The stage 185 is used to support and navigate the collection optics 190 so as to collect light from the DUT 130. The collection optics may include an objective lens and a solid immersion lens (SIL), in a manner known in the art. The various elements of the emission tester are controlled by a controller 195 via connector 120, which may be a general purpose computer pre-programmed to perform specific tasks.

As can be understood, for maximum light collection efficiency, the inspected surface of the DUT 130 needs to be orthogonal to the optical axis of the collection optics 190. To achieve that, the tilt mechanism 165 is operated so as to tilt the adapter plate 155 as shown by the double-headed arrow, so as to achieve the required alignment. In FIG. 1A the adapter plate 155 is shown leveled with the tabletop 175, while in FIG. 1B the adapter plate 155 is shown tilted with respect to the tabletop 175. However, while the tilt mechanism 165 is operable to tilt the adapter plate 155, as shown in FIG. 1B the tester head 110 is stationary and does not move with the adapter plate 155. Therefore, in the prior art, a flexible connector 115 is used to maintain the connections between the tester head 110 and the DUT 130. However, the use of such a flexible adapter introduces several drawbacks to such an arrangement. Such flexible adapters are complex and expensive. Additionally, in order to obtain accurate testing, each such flexible adapter needs to be accurately characterized, which adds to the cost of the arrangement. Regardless of characterization, the flexible adapter may introduce inaccuracies into the testing. Moreover, the adapter may be exposed to repeated stresses due to repeated tilting and may fail prematurely.

Accordingly, there is a need in the art for a system that will allow docking of the tester head to the DUT without a flexible adapter, i.e., hard docking, while still maintain the ability to align the DUT to the optical axis of the collection optics.

SUMMARY OF THE INVENTION

The present inventors provide an apparatus and method for hard-docking of a tester head to a DUT, while permitting the angular alignment of a specimen to be inspected to the optical axis of an optical testing tool.

In one aspect of the invention, a system for orthogonal alignment of a specimen to an optical axis of a collection optics is provided. The system comprises a self-leveling tabletop; a specimen holder coupled to the tabletop and held at a fix orientation; collection optics coupled to the tabletop; a plunger coupled to the tabletop and operable to maintain the leveling orientation of the tabletop; a control valve sensing the leveling orientation of the tabletop and coupled to the plunger to control the operation of the plunger; and an aligner coupled to the tabletop and operable to change the alignment of the optical axis of the collection optics with respect to the specimen without changing the fixed orientation of the specimen holder.

In various illustrative implementations the aligner is structured as a blocking valve operable to block the operation of the control valve, and a tilting mechanism coupled between the tabletop and the specimen holder. The tilting mechanism can be implemented as a plurality of electrical motors. According to another implementation the aligner is structured as several lifters, each coupled to the plungers and the tabletop. According to yet another implementation, the aligner is structured as a tilt stage supporting the collection optics. By "tilt stage" what is meant is a stage that allows changing the angular alignment of the optical axis with respect to the specimen, in contrast with a stage that allows navigation in the plane of the specimen and distance therefrom. According to another implementation the collection optics is coupled to a holder and the holder comprises rotation mechanism that allows changing the angular alignment of the optical axis with respect to the specimen.

Various embodiments of the invention also provide for a method for orienting an optical system with respect to a specimen. The method is particularly useful for an optical system having a tabletop, collection optics coupled to the tabletop, and a specimen holder coupled to the tabletop. The method proceeds by placing the specimen in the specimen holder; fixing said specimen holder at a fixed orientation; and controlling the optical system so as to place the collection optics in an orientation such that the optical axis of the collection optics is perpendicular to an area of interest on the specimen without disturbing the fixed orientation of the specimen holder. In one example, the process of controlling the optical system is implemented by tilting the tabletop. According to another example the process of controlling the optical system is implemented by tilting the collection optics. When a solid immersion lens is used, once the appropriate tilting has been achieved, the SIL is made to contact the specimen.

In a more specific implementation, a system for testing an integrated circuit (IC) stimulated to simulate operating conditions is provided. The system includes a tabletop; a specimen holder coupled to the tabletop. The IC is mounted onto the specimen holder; a collection optics arrangement is coupled to the tabletop; an adapter is provided for hard-docking a tester head to the IC and thereby hold the specimen holder in a fixed orientation; an aligner is coupled to the tabletop and is operable to change the alignment of the optical axis of the collection optics with respect to the IC without changing the fixed orientation of the specimen holder.

In various implementations the system may further include a plurality of plungers coupled to the tabletop and operable to maintain the leveling orientation of the tabletop, and a plurality of control valves each sensing the leveling orientation of the tabletop and coupled to respective one of the plungers to control the operation of the plunger. The system may also include blocking valves, each operable to block the operation of a respective control valve, and a tilting mechanism coupled between the tabletop and the specimen holder. The tilting mechanism may be implemented as a plurality of electrical motors, such as stepper motors or servomotors. The tiltable holder can be implemented as a test bench having lifter system operable to adjust the tilt of the test bench, and the lifter system may be implemented as a plurality of lifters and a plurality of motors, each of the motors coupled to a respective lifter. The aligner may further be implemented as a plurality of lifters coupled to respective plungers, or as a tilt stage supporting the collection optics.

The invention is described herein with reference to particular embodiments thereof, which are exemplified in the drawings. It should be understood, however, that the various embodiments depicted in the drawings are only exemplary and may not limit the invention as defined in the appended claims.

DETAILED DESCRIPTION

An embodiment of the invention will now be described in details with reference to FIGS. 2A and 2B and, for illustration purposes, it will be depicted as implemented in the system of FIGS. 1A and 1B. Such a system is particularly useful for photon emission testing of integrated circuits. Since photon emission from integrated circuits is very faint, the system described with respect to FIGS. 2A and 2B uses a SIL. However, those skilled in the art can readily observe that the invention can be easily implemented in other optical systems that may or may not use a SIL.

Figure 2A:
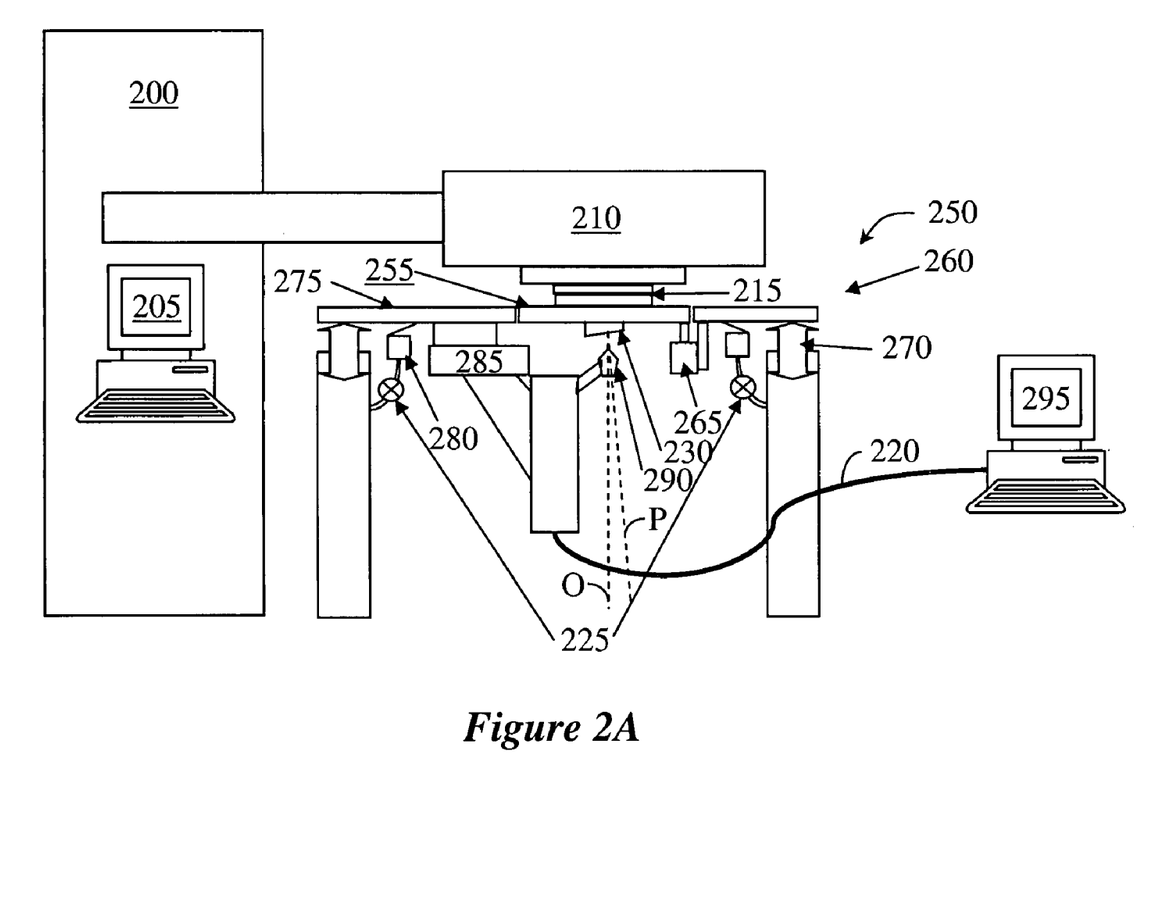
FIGS. 2A and 2B depict an embodiment of the invention as implemented in the system of FIGS. 1A and 1B.
Figure 2B:
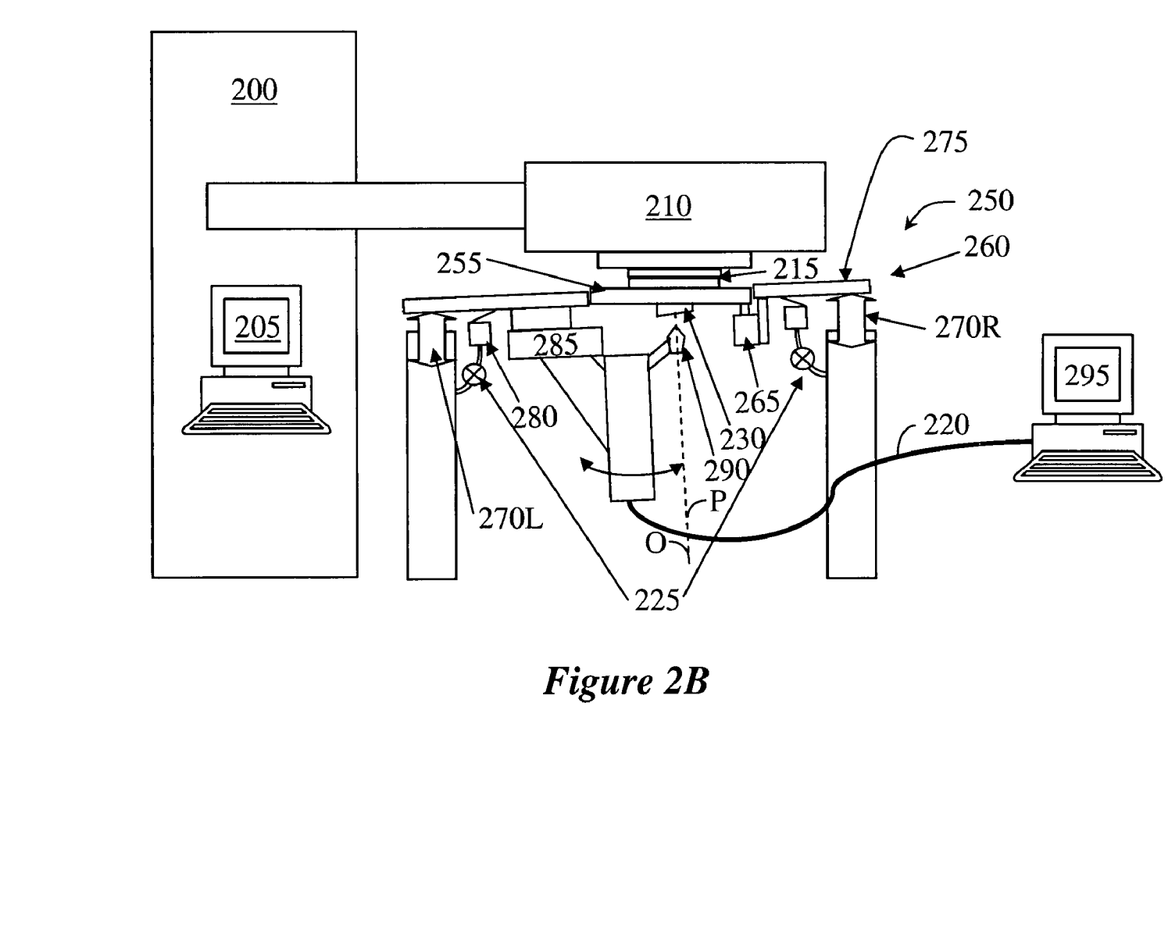

In FIGS. 2A and 2B, elements that are the same or similar to those in FIGS. 1A and 1B have the same enumeration, except that it's in the two-hundreds rather than the one-hundred series. To illustrate the problem solved by the invention, the DUT 230 is depicted in FIGS. 2A and 2B as having a slanted surface. Consequently, the surface of the DUT 230 is not perpendicular to the optical axis of the collection optics 290. This is illustrated by dashed line "P", which represents a line perpendicular to the surface of the DUT 230, and dashed line "O", which represents the optical axis of collection optics 290. Of course, the invention is also helpful in other circumstances, such as when the surface of the DUT is irregular and a localized area to be investigated is not perpendicular to the optical axis of the collection optics 290.

In the embodiment of FIGS. 2A and 2B, a blocking valve 225 is inserted in each line of each level control valve 280. Each of the blocking valve 225 may be manually or remotely controlled. If the blocking valve is remotely controlled, it can be connected to the controller 295 to be controlled according to the program run by the controller 295. The function of the blocking valve 225 is to block the operation of the control valve 280 and decouple it from the plunger 270. When the blocking valve 225 is in the open position, the level control valve 280 is coupled to the plunger 270 and operates to maintain leveling of the tabletop 275. On the other hand, when the blocking valve is in the close position, the level control valve 280 cannot change the pressure applied to the plunger 270 and, consequently, the plunger 270 does not maintain the tabletop at a level position.

More specifically, as is known in the prior art, a self-leveling pneumatic tabletop uses air pressure to maintain the tabletop at a level position. For example, the tabletop may rest on four plungers, each of which may be connected to a control valve. When a weight is placed on one side of the table and disturbs the tabletop's equilibrium, the disturbance is sensed by the control valves, which then change the pressure inside the plunger so as to return the tabletop to a level position. In normal operation, the tabletop is allowed to automatically maintain its level position and the stage 285 is used to navigate the collection optics 290 so that the appropriate area of the DUT 230 can be inspected. However, as explained previously, sometimes the area to be inspected is not level or not aligned perpendicularly to the optical axis of the collection optics 290. Such a situation causes a reduction in the image quality as well as the collection efficiency of the collection optics 290. To overcome this problem the angular orientation between the DUT 230 and the collection optics 290 needs to be changed.

In the prior art the angular orientation between the DUT and the collection optics is changed by tilting the adapter plate using the tilting mechanism, which, as explained before, required the use of a flexible adapter. According to this embodiment of the invention, on the other hand, no flexible adapter is used, but rather, the tester head 210 is hard-docked to the adapter plate 255. By hard-dock it is meant that once the tester head is docked to the DUT, no relative motion is allowed between the DUT and the tester head. Therefore, for hard-docking the tester head to the DUT the user may use a rigid 215, rather than a flexible connector such as connector 115.

According to an illustrative method of the invention, after the tester head 210 is hard-docked to the adapter plate 255 and the tabletop has been stabilized in the level position, the blocking valves 225 are actuated so as to assume to closed position. Under this condition, the tabletop 275 is counter-balanced by pressurized plungers 270, which makes it very easy to tilt the tabletop 275. However, if the tabletop 275 is tilted, the plungers 270 will not correct the tilt, since the conduits from the control valves 280 are blocked by the blocking valves 225. Therefore, when the tilting mechanism 265 is actuated to change the angular orientation between the DUT 230 and the collection optics 290, the tabletop 275, rather than the adapter plate 255 is tilted. This is because the adapter plate 255 is held in its position by the hard-dock to the tester head 210, while the tabletop 275 is easily moved since it is riding on pressurized plungers 270. This tilt position is demonstrated in FIG. 2B.

As can be appreciated by comparing FIGS. 2A and 2B, in FIG. 2A the tilting mechanism 265 is in a somewhat extended position. The tabletop is maintain level by the plungers 270, two of which are shown in the Figures, and both of which are shown as extending to the same extent. On the other hand, in FIG. 2B the tilt mechanism 265 has been pulled to reduce its extension. Consequently, the tabletop 275 is tilted by the right plunger 270R extending, while the left plunger 270L compressing. The adapter plate 255 has not moved as it is hard docked to the tester head 210. Accordingly, a change in the angular orientation between the DUT 230 and the collection optics 290 has been achieved as is illustrated by the two dashed lines "P" and "O" coinciding in FIG. 2B.

Figure 3A:
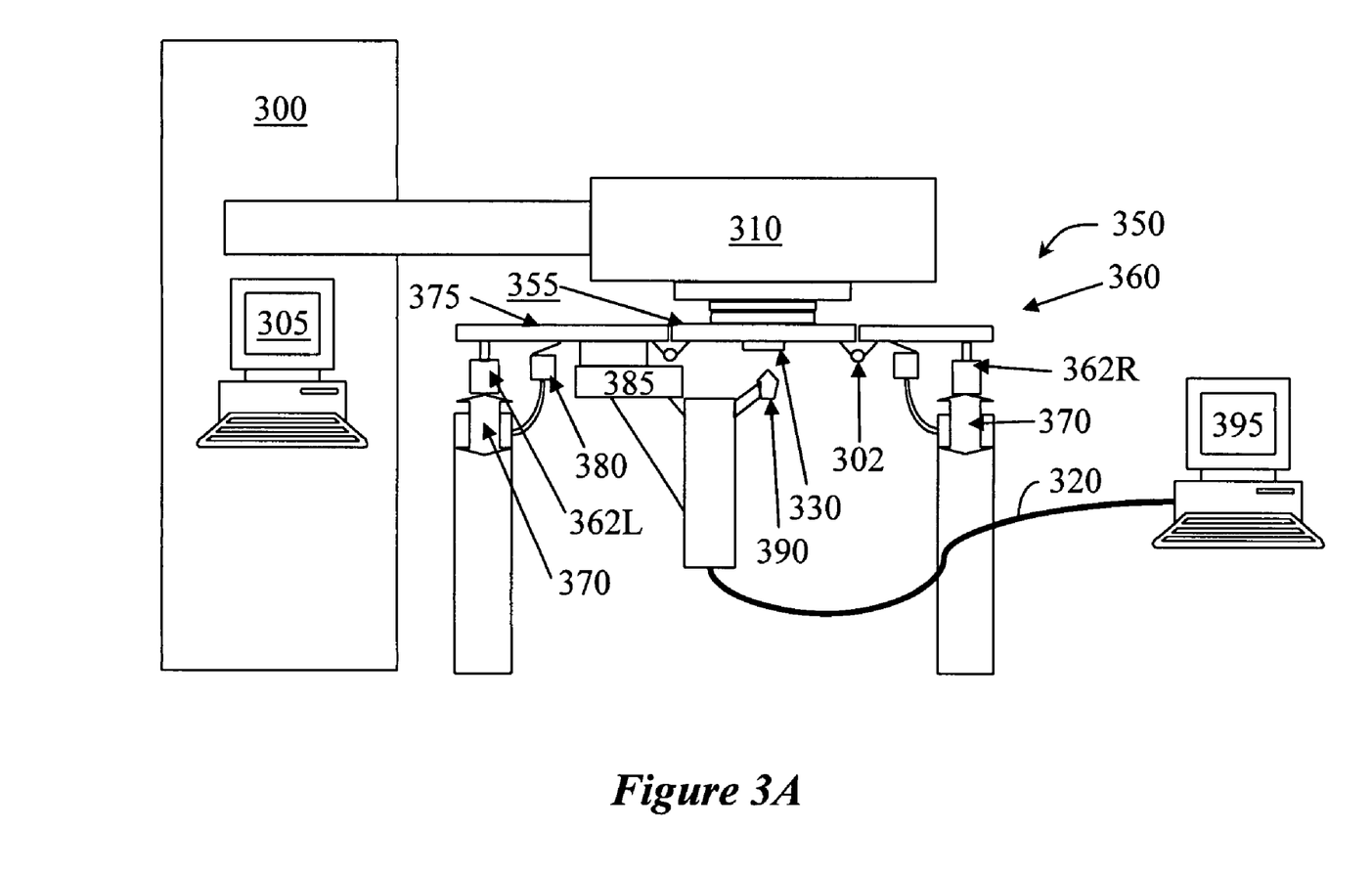
FIGS. 3A and 3B depict another embodiment of the invention as implemented in the system of FIGS. 1A and 1B.
Figure 3B:
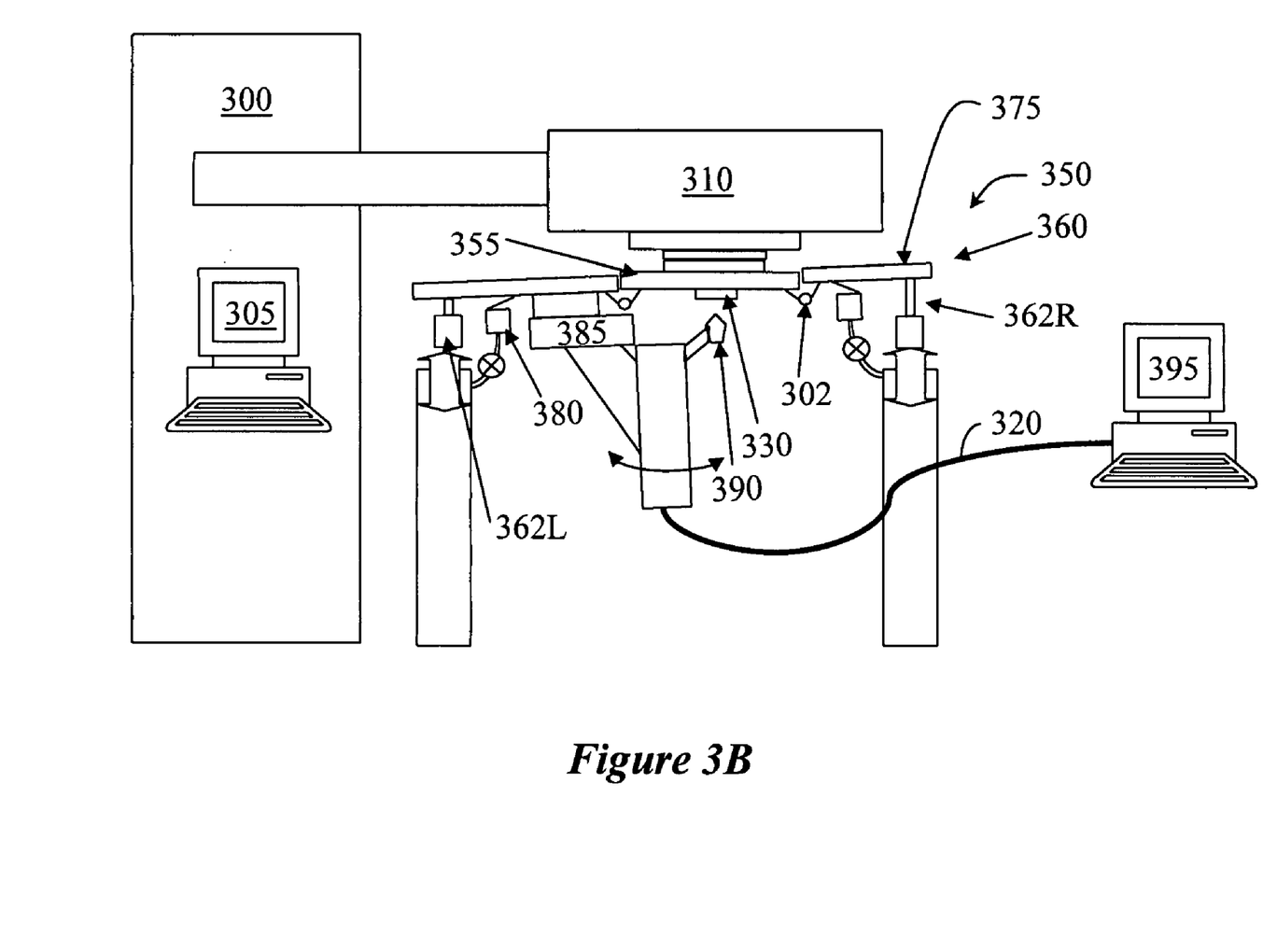

FIGS. 3A and 3B depict another embodiment of the invention. For illustration purposes, this embodiment is depicted as implemented in the system of FIGS. 1A and 1B. Also, elements that are the same or similar to those in FIGS. 1A and 1B have the same enumeration, except that it's in the three-hundreds rather than the one-hundred series. In the embodiment of FIGS. 3A and 3B, the adapter plate 355 is connected to the tabletop 375 via elastic connection 302. By elastic it is meant that the connection allows for relative motion between the adapter plate 355 and the tabletop 375. Such connection may be, for example, a bellow arrangement, a bearing arrangement, and the likes. Elevating mechanism 362R and 362L are provided on top of plungers 370. While only two elevating mechanisms are shown, it would be appreciated that a different number may be used. For example, one elevating mechanism can be provided on each plunger so that if four plungers are used, four elevating mechanisms are used. The elevating mechanism may be manually of remotely controlled. If remote control is desired, the elevating mechanism may be a servomotor connected to the controller 395.

In the embodiment of FIGS. 3A and 3B, when a change in the angular orientation between the DUT and the collection optics is needed, the elevation mechanisms 362 are activated so as to tilt the tabletop 375, while the adapter plate 355 remains connected to the tester head 310 in a hard-dock manner. This is shown in FIG. 3B, wherein elevating mechanism 362R is extended while elevating mechanism 362L is contracted, so that the tabletop 375 is tilted.

Figure 4A:
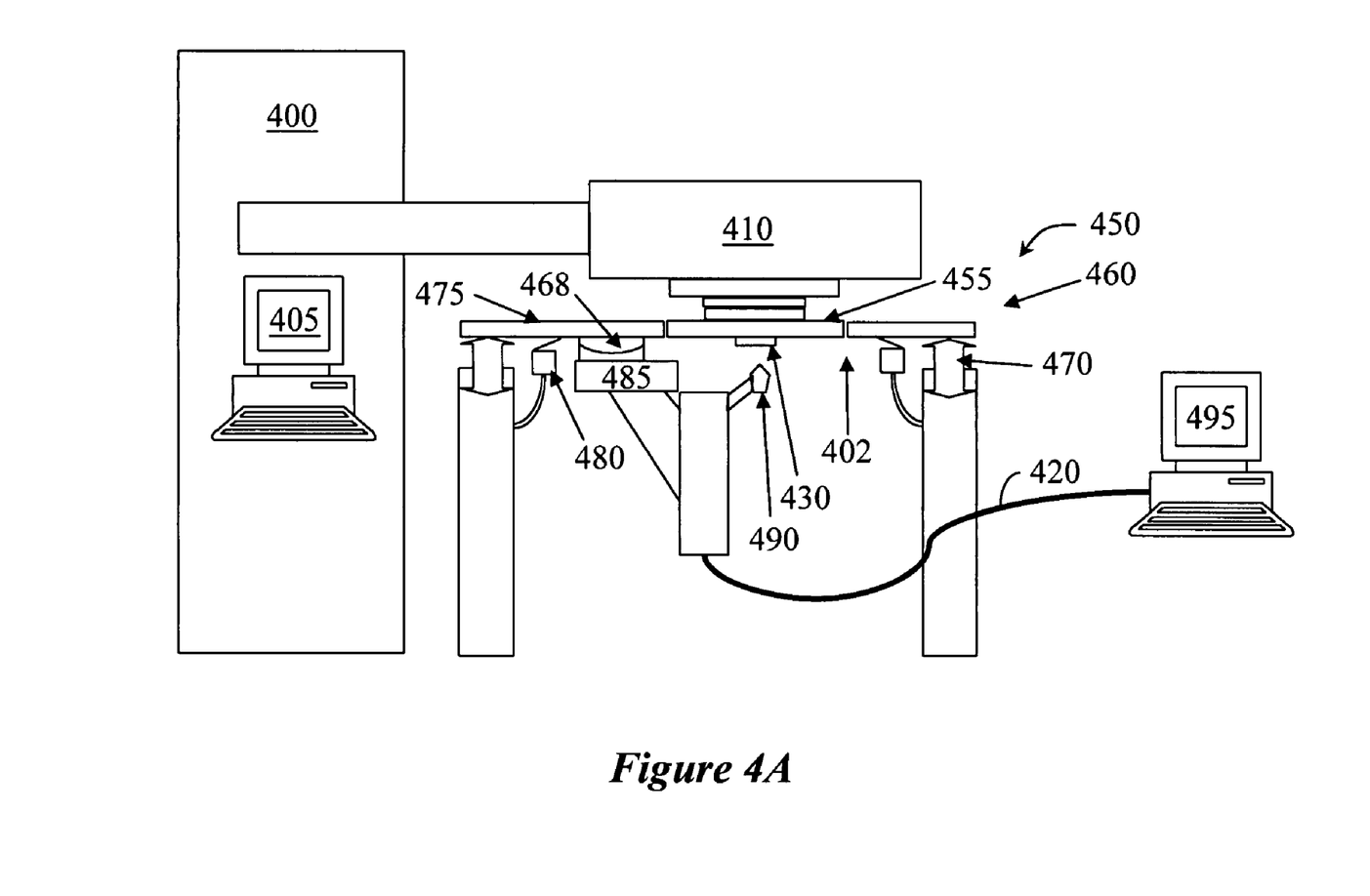
FIGS. 4A and 4B depict another embodiment of the invention as implemented in the system of FIGS. 1A and 1B.
Figure 4B:
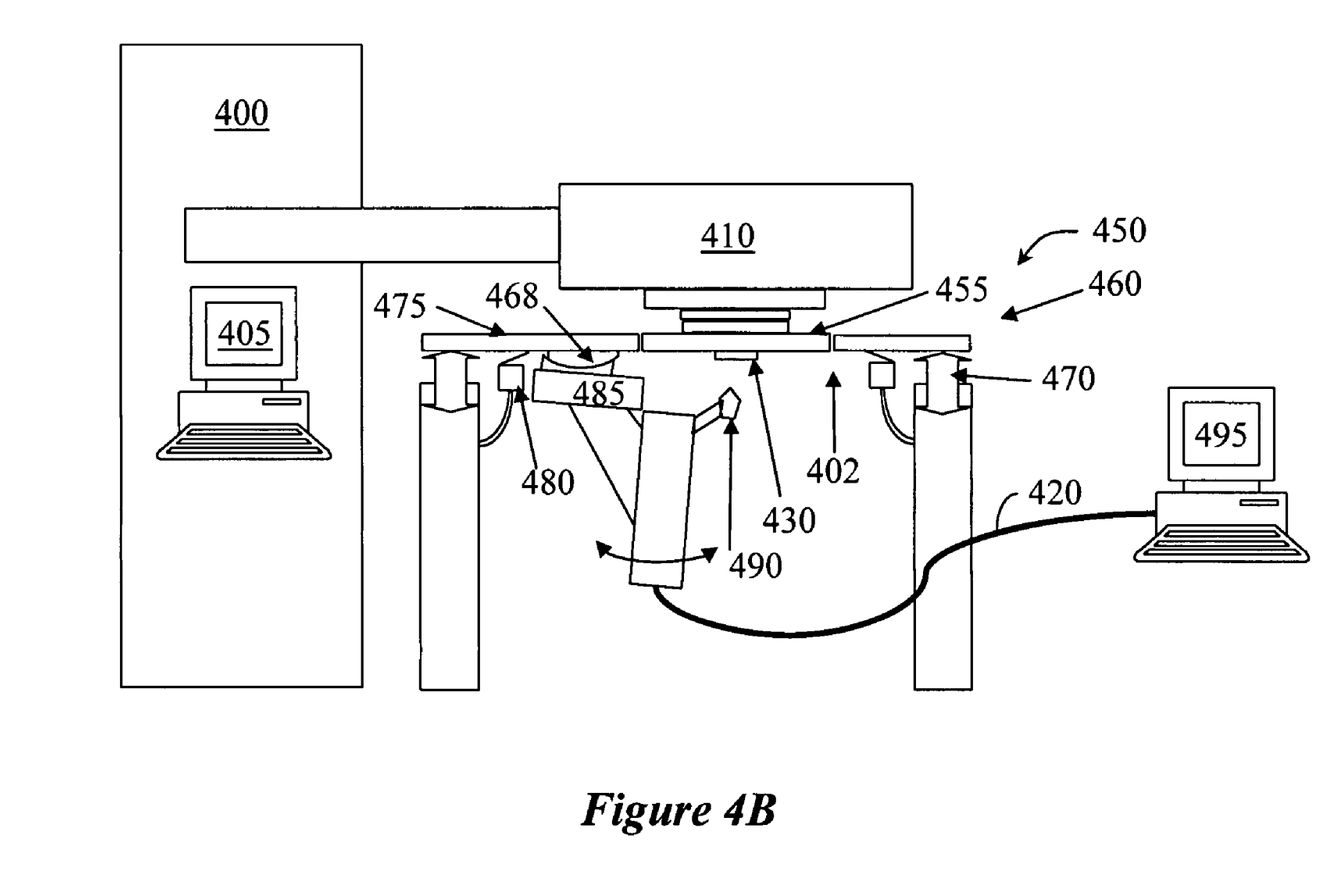

FIGS. 4A and 4B depict another embodiment of the invention. For illustration purposes, this embodiment is depicted as implemented in the system of FIGS. 1A and 1B. Also, elements that are the same or similar to those in FIGS. 1A and 1B have the same enumeration, except that it's in the four-hundreds rather than the one-hundred series. In the embodiment of FIGS. 4A and 4B, the adapter plate 455 is rigidly connected to the tabletop 475, so that no relative motion is allowed. For example, the adapter plate 455 may be bolted to the tabletop 475. As also shown, the x-y-z stage 485 is provided with an additional motion element 468, such as, e.g., an R-Theta stage. The motion element 468 enables moving the collection optics 490 so as to change the angular orientation of the collection optics 490 with respect to the DUT 430. This is depicted in FIG. 4B, wherein the motion element 468 is activated to move the collection optics 490 is exemplified by the double-headed arrow. As can be understood, due to the two-dimensional nature of the drawing, only one motion element 468 is shown, providing angular motion in the plane of the page. However, a second element may be provided in order to allow for angular motion in the plane perpendicular to the page, i.e., in and out of the page.

Figure 5A:
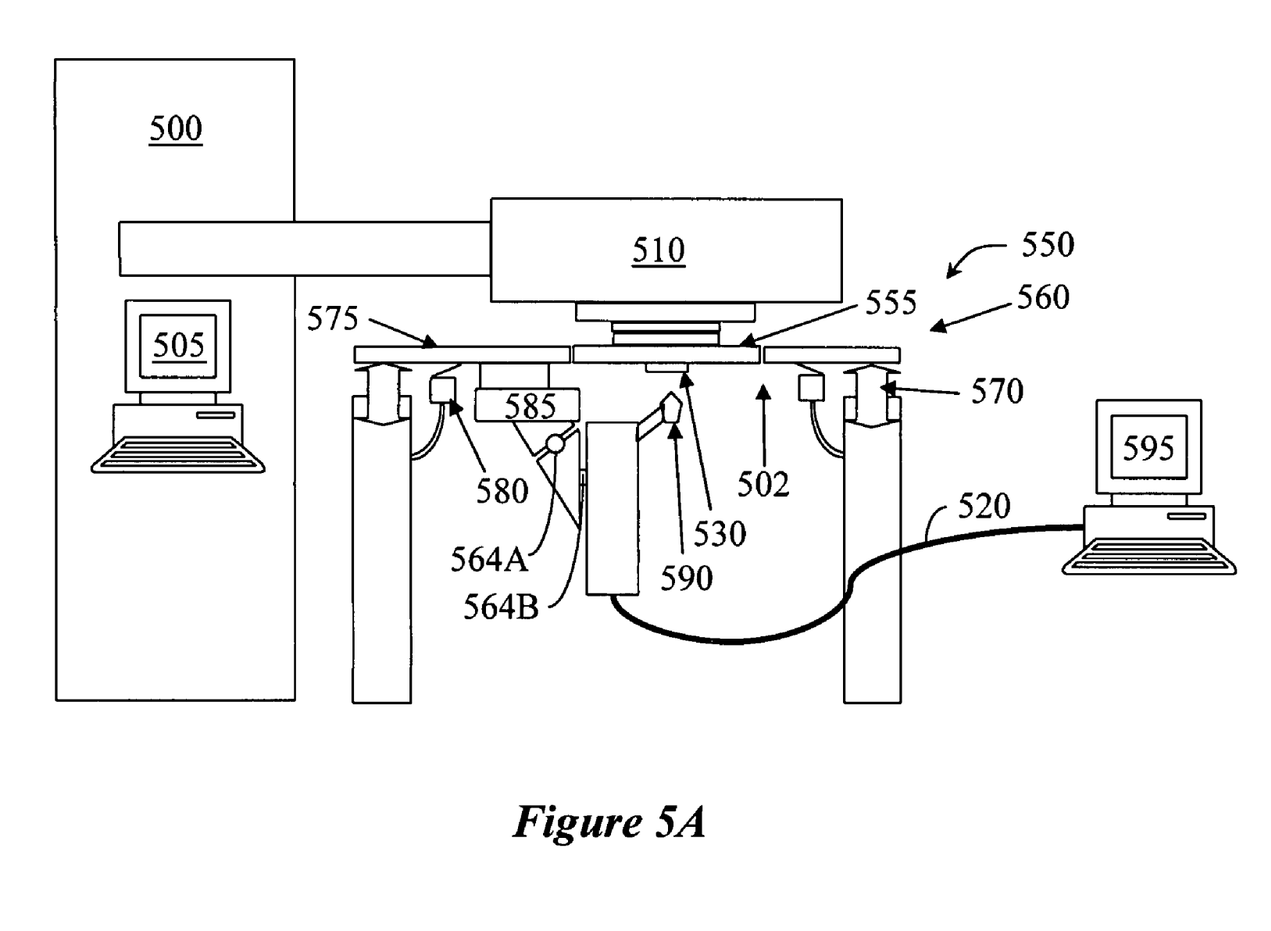
FIGS. 5A and 5B depict another embodiment of the invention as implemented in the system of FIGS. 1A and 1B.
Figure 5B:
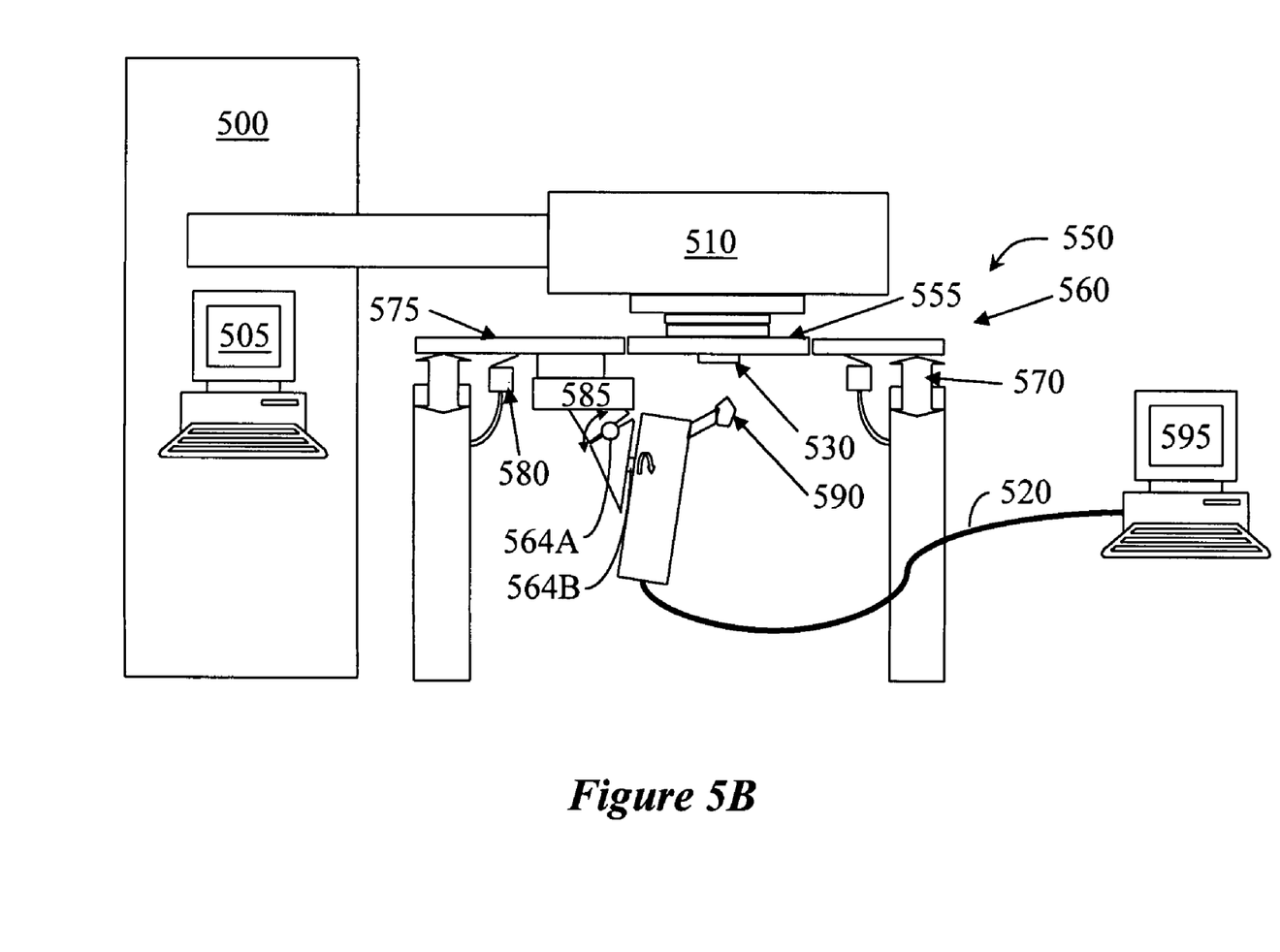

FIGS. 5A and 5B depict another embodiment of the invention. For illustration purposes, this embodiment is depicted as implemented in the system of FIGS. 1A and 1B. Also, elements that are the same or similar to those in FIGS. 1A and 1B have the same enumeration, except that it's in the five-hundreds rather than the one-hundred series. In the embodiment of FIGS. 5A and 5B, the adapter plate 555 is rigidly connected to the tabletop 575, so that no relative motion is allowed. For example, the adapter plate 555 may be bolted to the tabletop 575. The embodiment of FIGS. 5A and 5B is similar to that of FIGS. 4A and 4B in that additional degrees of motion are provided to enable better manipulation of the collection optics 590.

In the embodiment of FIGS. 5A and 5B two rotational elements, 564A and 564B, are provided on the support of the collection optics 590. The rotational elements 564A and 564B may be manually of remotely controlled. If remote control is desired, the rotational elements 564A and 564B may be stepper motors or servomotors connected to the controller 595. Using the x-y-z stage 585 the collection optics 590 can be placed in the appropriate spatial position to enable investigation of a particular area of the DUT 530. If the particular area of interest is not perpendicular to the optical axis of collection optics 590, one of both of the rotational elements 564A and/or 564B can be used to tilt the collection optics 590 so as to provide correction to the angular orientation, as shown by the arrows.

While the invention has been described with reference to particular embodiments thereof, it is not limited to those embodiments. Specifically, various variations and modifications may be implemented by those of ordinary skill in the art without departing from the invention's spirit and scope, as defined by the appended claims. Additionally, all of the above-cited prior art references are incorporated herein by reference.

What is claimed is:

1. A system for orthogonal alignment of a specimen to an optical axis of a collection optics, comprising:
   a self-leveling tabletop;
   a specimen holder coupled to said tabletop and held at a fixed orientation;
   collection optics coupled to said tabletop;
   a plunger coupled to said tabletop and operable to maintain the leveling orientation of said tabletop;
   a control valve sensing the leveling orientation of said tabletop and coupled to said plunger to control the operation of said plunger; and
   an aligner coupled to said tabletop and operable to change an angular alignment of said optical axis of said collection optics with respect to said specimen without changing said fixed orientation.

2. The system of claim 1, wherein said aligner comprises a blocking valve operable to block the operation of said control valve, and a tilting mechanism coupled between said tabletop and said specimen holder.

3. The system of claim 2, wherein said tilting mechanism comprises a plurality of electrical motors.

4. The system of claim 1, wherein said aligner comprises lifters coupled to said plunger.

5. The system of claim 1, wherein said aligner comprises a tilt stage supporting said collection optics.

6. The system of claim 1, wherein said collection optics is coupled to a holder and wherein said holder comprises rotation mechanism.

7. The system of claim 6, wherein said rotation mechanism comprises electrical motor.

8. The system of claim 1, wherein said collection optics comprise a solid immersion lens.

9. A method for orienting an optical system with respect to a specimen, the optical system having a tabletop, collection optics coupled to said tabletop, and a specimen holder coupled to said tabletop, the method comprising:
   placing the specimen in the specimen holder;
   fixing said specimen holder at a fixed orientation; and
   controlling said optical system so as to place said collection optics in an orientation such that the optical axis of said collection optics is perpendicular to an area of interest on said specimen without changing said fixed orientation,
   wherein the controlling said optical system includes changing an angular alignment of the optical axis of said collection optics.

10. The method of claim 9, wherein said controlling comprises tilting said tabletop.

11. The method of claim 9, wherein said controlling comprises tilting said collection optics.

12. The system of claim 9, wherein said collection optics comprises a solid immersion lens and the method further comprises placing said solid immersion lens in contact with said specimen.

13. A system for testing an integrated circuit (IC) stimulated to simulate operating conditions, comprising:
   a tabletop;
   a specimen holder coupled to said tabletop, said IC connected to said specimen holder;
   collection optics coupled to said tabletop;
   an adapter for hard-docking a tester head to said IC and thereby holding said specimen holder in a fixed orientation; and
   an aligner coupled to said tabletop and operable to change an angular alignment of the optical axis of said collection optics with respect to said IC without changing said fixed orientation.

14. The system of claim 13, further comprising:
   a plurality of plungers coupled to said tabletop and operable to maintain the leveling orientation of said tabletop;
   a plurality of control valves each sensing the leveling orientation of said tabletop and coupled to respective one of said plungers to control the operation of said plunger.

15. The system of claim 14, wherein said aligner comprises a plurality of blocking valves each operable to block the operation of a respective control valve, and a tilting mechanism coupled between said tabletop and said specimen holder.

16. The system of claim 15, wherein said tilting mechanism comprises a plurality of electrical motors.

17. The system of claim 15, wherein said tilting mechanism comprises a test bench having lifter system operable to adjust the tilt of said test bench, said lifter system comprises a plurality of lifters and a plurality of motors, each of said motors coupled to a respective lifter.

18. The system of claim 14, wherein said aligner comprises a plurality of lifters coupled to respective plungers.

19. The system of claim 14, wherein said aligner comprises a tilt stage supporting said collection optics.

20. The system of claim 14, wherein said collection optics is coupled to a holder and wherein said holder comprises rotation mechanism.

21. A system for alignment of an inspected surface of a specimen to be orthogonal to an optical axis of a collection optics, the system comprising:
   a tester head;
   a tabletop located at a distance from the tester head;
   an adapter plate hard-docked to the tester head through a rigid connector, the adapter plate fixed to the specimen leaving the inspected surface of the specimen exposed;
   collection optics coupled to the tabletop through an x-y-z stage and facing the inspected surface of the specimen;
   plungers coupled to the tabletop for operations of self-leveling and vibration-isolating the tabletop;
   level control valves coupled to the plungers for controlling the plungers;
   blocking valves coupled to the level control valves and capable of blocking the level control values from controlling the plungers; and
   an optical axis control mechanism for changing an orientation of the collection optics with respect to the tester head to obtain alignment of the optical axis with an axis orthogonal to the inspected surface of the specimen while keeping the adapter plate in a fixed position,
   wherein the optical axis control mechanism is selected from a group consisting of:
      a tilting mechanism coupling the tabletop to the adapter plate, the tilting mechanism operable to tilt the tabletop, when the blocking valves are blocking the level control valves,
      an elastic connection coupling the tabletop to the adapter plate and elevating mechanisms located between the plungers and the tabletop, the elevating mechanisms operable to tilt the tabletop by elevating the tabletop above some but not all of the plungers, when the blocking valves are blocking the level control valves, and
      one or more rotational elements coupled between the collection optics and the tabletop, the rotational elements operable to rotate the optical axis.

* * * * *